United States Patent [19]

Danno et al.

[11] Patent Number: 4,891,122
[45] Date of Patent: Jan. 2, 1990

[54] AIR FUEL RATIO DETECTING DEVICE

[75] Inventors: Yoshiaki Danno; Takashi Dogahara, both of Kyoto, Japan

[73] Assignee: Misubishi Jidosha Kogyo Kabushiki Kaisha, Tokyo, Japan

[21] Appl. No.: 933,850

[22] Filed: Nov. 24, 1986

[30] Foreign Application Priority Data

Nov. 22, 1985 [JP] Japan .................. 60-262982

[51] Int. Cl.⁴ ........................................... G01N 27/56
[52] U.S. Cl. .................... 204/406; 204/412; 204/425; 204/427
[58] Field of Search ............... 204/406, 412, 425, 426, 204/427, 410, 411

[56] References Cited

U.S. PATENT DOCUMENTS

| | | | |
|---|---|---|---|
| 4,440,621 | 4/1984 | Kitahara et al. | 204/406 |
| 4,578,171 | 3/1986 | Yamada | 204/406 |
| 4,586,476 | 5/1986 | Asayama | 204/406 |
| 4,591,421 | 5/1986 | Yamada | 204/406 |
| 4,594,139 | 6/1986 | Asayama et al. | 204/406 |
| 4,601,809 | 7/1986 | Kitahara | 204/406 |
| 4,615,787 | 10/1986 | Yamada | 204/406 |
| 4,629,549 | 12/1986 | Kojima et al. | 204/406 |
| 4,718,999 | 1/1988 | Suzuki | 204/406 |

Primary Examiner—John F. Niebling
Assistant Examiner—Ben C. Hsing
Attorney, Agent, or Firm—Schwartz & Weinrieb

[57] ABSTRACT

The invention provides a device for detecting an air fuel ratio of an air fuel mixture supplied to the combustion apparatus of an internal combustion engine. The device comprises a sensor cell for developing an electric signal in response to the difference between the concentration of oxygen an exhaust gas and the concentration of oxygen in a reference gas, a controlling means for developing an electric control signal having a polarity determined from an output of the sensor cell, a pump cell for moving oxygen ions in response to an electric control signal received from the controlling means, a control current detecting means for detecting control current flow between the controlling means and the pump cell, an air fuel ratio detecting means for detecting the air fuel ratio from the control current flow, and a stoichiometric air fuel ratio detecting means for detecting the direction of the control current flow so as to determine the stoichiometric air fuel ratio.

7 Claims, 3 Drawing Sheets

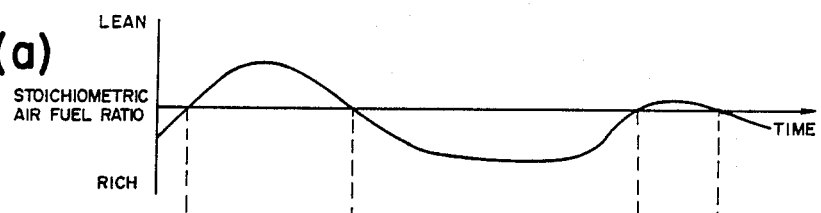
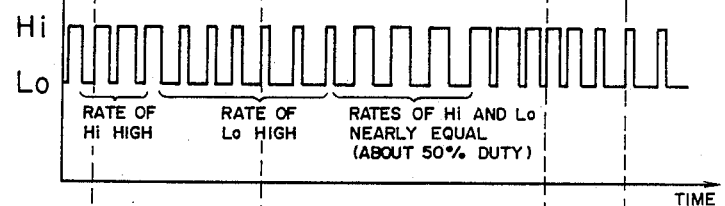
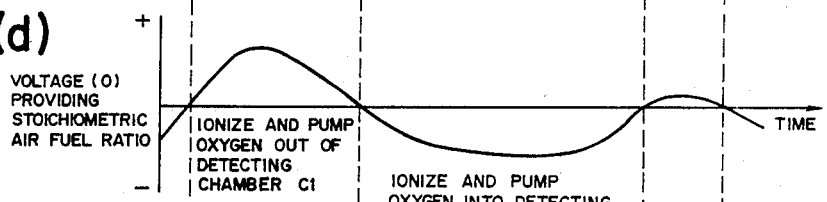
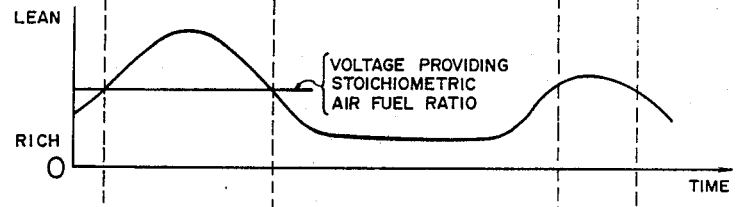
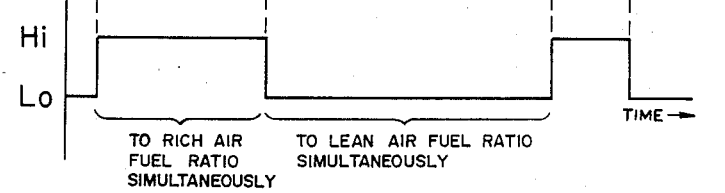

AIR FUEL RATIO DETECTING DEVICE

FIELD OF THE INVENTION

This invention relates to a device for detecting the air fuel ratio of an air fuel mixture supplied to a combustion apparatus of an internal combustion engine.

BACKGROUND OF THE INVENTION

Various air fuel ratio detecting devices have been proposed which make use of characteristics of the oxygen concentration cell action and the oxygen ion pumping action of zirconia as disclosed, for example, in Japanese patent laid-open No. 56-130649. Use of an air fuel ratio detecting device of the type disclosed allows detection of a wide range of air fuel ratios.

However, the accuracy of such a conventional air fuel ratio detecting device is not sufficiently high as to allow the air fuel ratio detecting device to be used for detecting the stoichiometric air fuel ratio, for example, for a ternary catalyzer, due to its structure.

OBJECT OF THE INVENTION

It is therefore an object of the present invention to provide an air fuel ratio detecting device which can detect the stoichiometric air fuel ratio of an air fuel mixture with high degree of accuracy.

SUMMARY OF THE INVENTION

In order to attain the foregoing and other objects, according to the present invention, there is provided an air fuel ratio detecting device, comprising: a sensor cell for developing an electric signal in response to the difference between the concentration of oxygen in the exhaust gas after the air fuel mixture has been burned in a combustion chamber and the concentration of oxygen in a reference gas; a controlling means for developing an electric control signal having a polarity determined from the output of the sensor cell; a pump cell for moving oxygen ions in response to an electric control signal received from the controlling means; a control current detecting means for detecting control current flow transferred between the controlling means and said pump cell; and an air fuel ratio detecting means for detecting the air fuel ratio from the control current flow detected by said control current detecting means.

In the air fuel ratio detecting device according to the present invention, the sensor cell develops an electric signal in response to the difference between a concentration of oxygen in the exhaust gas after combustion of the air fuel mixture and a concentration of oxygen in a reference gas, and the controlling means develops an electric control signal of a polarity determined from the output of the sensor cell. The electric control signal is delivered to the pump cell, and thus the pump cell causes oxygen ions to move in response to the electric control signal whereupon air fuel ratio information which is transferred between the controlling means and the pump cell is detected by the air fuel ratio detecting means. Accordingly, the air fuel ratio detecting device according to the present invention is advantageous in that it can detect the stoichiometric air fuel ratio with a high degree of accuracy and high a high degree of responsiveness.

Various other objects, features, and attendant advantages of the present invention will become more apparent when considered in conjunction with the accompanying drawings, in which like reference characters are used to designate corresponding parts throughout the several views, and wherein:

BRIEF DESCRIPTION OF THE DRAWINGS

FIGS. 2, 3 and 4(a) to 4(f) are graphs illustrating operation of the air fuel ratio detecting device of FIG. 1.

DETAILED DESCRIPTION OF THE PREFERRED EMBODIMENTS

Figure 1:
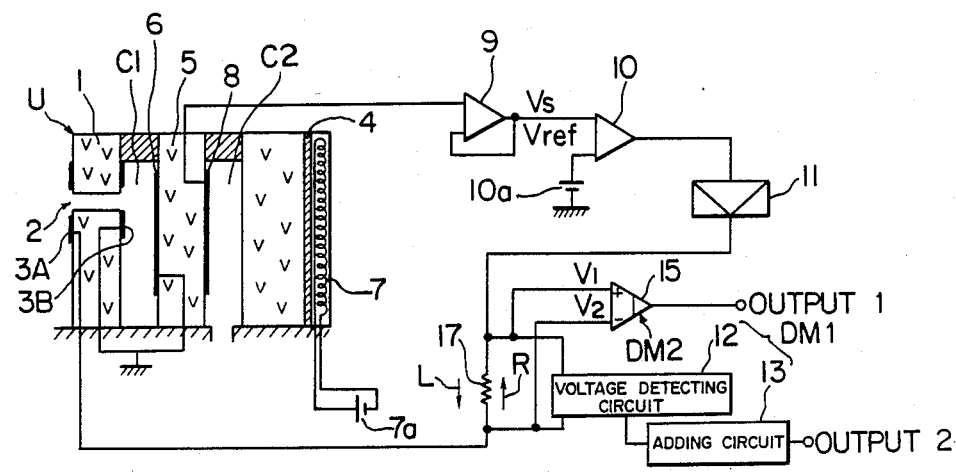
FIG. 1 is a diagrammatic representation illustrating an entire construction of an air fuel ratio detecting device according to a preferred embodiment of the present invention.

Referring first to FIG. 1, an air fuel ratio detecting device according to a preferred embodiment of the present invention comprises a cell unit U which includes a sensor cell 5, a pump cell 1, a heater 7, and other elements to be described in more detail later, and is located adjacent a path of exhaust gas of an internal combustion engine.

Now, the structure of the cell unit U will be described in detail. Zirconia is used for the sensor cell 5, and the sensor cell 5 is located such that one of the opposite walls thereof is opposed or exposed to a detecting chamber (cavity) C1 into which exhaust gas is introduced through a diffusion hole 2 and which cooperates with the diffusion hole 2 to constitute a diffusion control means, while the other wall thereof is opposed or exposed to an atmospheric chamber C2 into which the atmosphere (air) as a reference gas is introduced. A sensor electrode 6 is located on the wall of the sensor cell 5 adjacent the detecting chamber C1 and a reference electrode 8 is located on the other wall adjacent the atmospheric chamber C2. It is to be noted that the sensor electrode 6 and the reference electrode 8 are made of platinum and each has a large number of fine holes or pores formed therein.

Figure 3:
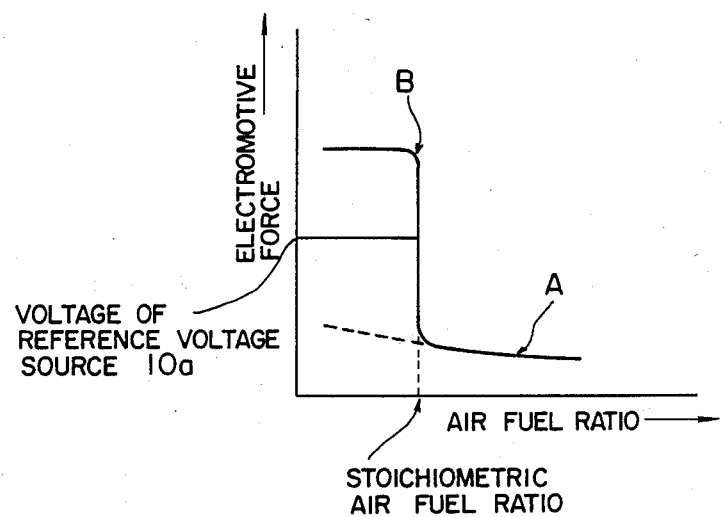

With such a construction as described above, an electric signal (electromotive force) appears between the electrodes 6, 8 of the sensor cell 5 in response to a difference between the concentration of oxygen in the exhaust gas introduced into the detecting chamber C1 and the concentration of oxygen in the atmosphere introduced into the atmospheric chamber C2, or in other words, in response to an air fuel ratio (refer to FIG. 3).

Zirconia is also used for the pump cell 1, and the pump cell 1 is located such that one of the opposite walls thereof is opposed to the detecting chamber C1 while the other wall thereof is opposed to the path of exhaust gas. A pair of pump electrodes 3A, 3B are located on the walls of the pump cell 1 and surround an entrance and an exit of the diffusion hole 2, respectively. Also the pump electrodes 3A, 3B are made of platinum and each has a large number of fine holes or pores formed therein.

The pump cell 1 operates such that when the pump electrode 3A is positive, it ionizes oxygen within the detecting chamber C1 and pumps it out into the path of the exhaust gas, but on the contrary when the pump electrode 3A is negative, it ionizes oxygen in the path of the exhaust gas and pumps it out into the detecting chamber C1.

It is to be noted that the diffusion hole 2 is in the pump cell 1 and defined as a throughbore provides for communications between the path of the exhaust gas and the detecting chamber C1.

The heater 7 is mounted on a partition wall on the side of the atmospheric chamber C2 which is opposite that of the sensor cell 5 with an insulator layer 4 interposed therebetween. Thus, as power is supplied from a power source 7a to the heater 7, the entire cell unit U is heated by the heater 7. Since the cell unit u is heated to a temperature, for example, of 600 to 700 degrees C., operation of the pump cell 1 and the sensor cell 5 is assured.

The sensor electrode 6 and the pump electrode 3B are grounded, and the reference electrode 8 is connected to an input terminal of a comparator 10 via an amplifier 9.

Connected to the other input terminal of the comparator 10 is a reference voltage source 10a the voltage of which corresponds to an electromotive force when the air fuel ratio of the mixture coincides with the stoichiometric air fuel ratio. Thus, the comparator 10 compares an output voltage Vs of the amplifier 9 with a reference value signal Vref of the reference voltage source 10a and outputs, when, for example, Vs≧Vref, a signal of a high level (hereinafter referred to as a "Hi signal") but outputs a signal of a low level (hereinafter referred to as a "Lo signal") when Vs<Vref.

The air fuel ratio detecting device further includes an integrating amplifier 11 with positive and negative power sources serving as a controlling means with an inversion-type power source and is connected within the system so as to receive a signal from the comparator 10. The integrating amplifier 11 with positive and negative power sources integrates a signal from the comparator 10 with a negative coefficient and outputs the same while the signal is a Hi signal, but on the contrary when the signal from the comparator 10 is a Lo signal, it integrates the signal with a positive coefficient and outputs the same.

In this manner, an electric control signal outputted from the integrating amplifier 11 with positive and negative power sources varies in polarity and duration in response to an output of the comparator 10 and its duration, respectively, and is supplied to the pump electrode 3A.

It is noted that, an electric control signal from the integrating amplifier 11 with positive and negative power sources contains information regarding a current air fuel ratio. Thus, an air fuel ratio detecting means is provided for detecting an air fuel ratio from control current flow which is transferred between the integrating amplifier 11 and the pump cell 1. The air fuel ratio detecting means includes a first detecting means (a linear air fuel ratio detecting means) DM1 for detecting the magnitude of the control current flow so as to determine a linear air fuel ratio, and a second detecting means (stoichiometric air fuel ratio detecting means) DM2 for detecting the direction of the control current flow so as to determine the stoichiometric air fuel ratio. In particular, an air fuel ratio detecting resistor 17 serving as a control current flow detecting means is interposed in a circuit for connection between the integrating amplifier 11 with positive and negative power sources and the pump electrode 3A of the pump cell 1. Signals $V_1$, $V_2$ from opposite ends of the resistor 17 are delivered to a comparator 15 of the second detecting means DM2.

The comparator 15 thus develops an output OUTPUT1 which is a Hi signal when $V_1 - V_2 \geq 0$ and which is a Lo signal when $V_1 - V_2 < 0$.

A voltage detecting circuit 12 for detecting a voltage across the resistor 17 is also provided as a component of the first detecting means DM1, and an adding circuit 13 which is also a component of the first detecting means DM1, is connected to the voltage detecting circuit 12 in order to add a bias value to an output of the voltage detecting circuit 12 so as to obtain an output OUTPUT2 which is always a positive value even if the output of the voltage detecting circuit 12 assumes a negative value.

With the construction described above, when an air fuel mixture supplied into a combustion chamber of the internal combustion engine is lean (or in other words, when a current air fuel ratio is higher than the stoichiometric air fuel ratio), an electromotive force corresponding signal Vs then obtained via the amplifier 9 from the electromotive force which is outputted from the sensor cell 5 and coincides with a value represented by the Nernst's formula is, as indicated at A in FIG. 3, lower than the reference voltage signal Vref, and hence a Lo signal is developed from the comparator 10. In this instance, an electric control signal having a positive value is developed from the integrating amplifier 11 with positive and negative power sources, and the electric control signal is delivered to the pump cell 1. Consequently, the potential at the pump electrode 3A becomes higher than that at the pump electrode 3B, and accordingly, oxygen within the detecting chamber C1 is ionized and pumped out of the detecting chamber C1 by the pump cell 1.

In this instance, current in the resistor 17 flows in a direction as indicated by an arrow mark L in FIG. 1, and hence $V_1 - V_2 > 0$. Accordingly, the output OUTPUT1 of the comparator 15 is a Hi signal.

The voltage across the resistor 17 is then detected by the voltage detecting circuit 12 and is biased by the adding circuit 13 so as to be outputted as an output OUTPUT2. In this instance, the output OUTPUT2 corresponds to a voltage value from the integrating amplifier 11 with positive and negative power sources. Accordingly, the output OUTPUT2 contains air fuel ratio information of to what degree the output OUTPUT2 is displaced toward the lean side from the stoichiometric air fuel ratio.

Continuing further, when the air fuel mixture changes from a lean state to a rich state (that is, from a state in which its air fuel ratio is higher than the stoichiometric air fuel ratio to another state in which its air fuel ratio is lower than the stoichiometric air fuel ratio), the electromotive force developed from the sensor cell 5 changes to a high value, as indicated at B in FIG. 3 when the air fuel ratio equals approximately the stoichiometric air fuel ratio due to a catalytic action of the electrodes (made of platinum) located on the sensor cell 5. Consequently, the signal Vs inputted into the comparator 10 becomes higher than the reference voltage signal Vref, which causes the output of the comparator 10 to change from a Lo signal to a Hi signal. As a result, an electric control signal having a negative value is developed from the integrating amplifier 11 with positive and negative power sources. As the electric control signal is delivered to the pump cell 1, the potential at pump electrode 3A becomes lower than the potential at the pump electrode 3B, and now, oxygen in the path of the exhaust gas is ionized and pumped into the detecting chamber C1.

Figure 2:
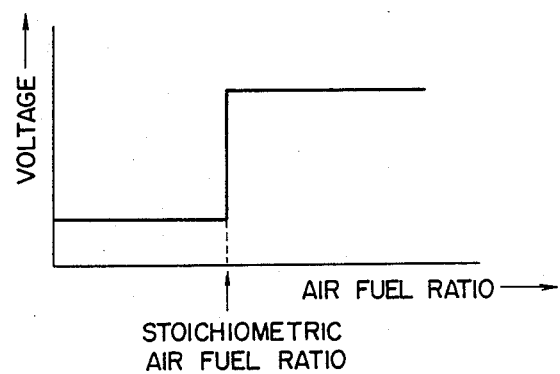

Thereupon, current flow in the resistor 17 is changed over to a direction as indicated by an arrow mark R in FIG. 1, and now $V_1 - V_2 < 0$. Consequently, the output OUTPUT1 of the comparator 15 is also changed over to a Lo signal. Since such change-over of the output OUTPUT1 of the comparator 15 from a Hi signal to a Lo signal occurs just at the stoichiometric air fuel ratio, if such change-over is detected, an air fuel ratio which coincides with the stoichiometric air fuel ratio can be detected. The output characteristic of the comparator 15 is illustrated in FIG. 2.

It is additionally noted that the voltage across the resistor 17 is then detected by the voltage detecting circuit 12 and is biased by the adding circuit 13 so as to be outputted as an output OUTPUT2. In this instance, the output OUTPUT2 corresponds to a voltage value from the integrating amplifier 11 with positive and negative power sources. Accordingly, the output OUTPUT2 contains air fuel ratio information of to what degree the output OUTPUT2 is displaced the rich side toward from the stoichiometric air fuel ratio.

It will be appreciated that reverse operation will occur when the air fuel ratio changes from a rich state to a lean state.

Accordingly, use of the information from the output OUTPUT2 can allow detection of the air fuel ratio over a wide range from the lean side to the rich side or vice versa.

It is to be noted that, in the case of a conventional $O_2$ sensor, a lean or rich atmosphere around an electrode cannot be suddenly changed into a rich or lean atmosphere when the air fuel ratio of air fuel mixture passes the stoichiometric air fuel ratio (from the lean side to the rich side or vice versa) because the electrode is surrounded by such a lean or rich atmosphere while, in the case of the air fuel ratio detecting device according to the present invention, the responsiveness is high and hence detection of an air fuel ratio which coincides with the stoichiometric air fuel ratio and accordingly detection of to what degree an air fuel ratio is displaced toward the lean or rich side from the stoichiometric air fuel ratio can be accomplished with a high degree of accuracy because the pump cell 1 operates so as to maintain the air fuel ratio of the air fuel mixture within the detecting chamber C1 of the cell unit U to a value equal to the stoichiometric air fuel ratio.

Changes in the air fuel ratio of the exhaust gas and general waveforms of the system of outputs of various elements of FIG. 1 are diagrammatically shown in FIGS. 4(a) to 4(f). When the air fuel ratio of the exhaust gas changes as shown in FIG. 4(a), waveforms of inputs Vs, Vref to the comparator 10 change as shown in FIG. 4(b). Here, a portion of the waveform Vs of FIG. 4(b) at which it exhibits a sudden change indicates that the air fuel ratio within the detecting chamber C1 coincides with the stoichiometric air fuel ratio. The waveform of the output of the comparator 10 is shown in FIG. 4(c) while the waveform of the output of the integrating amplifier 11 is shown in FIG. 4(d). The following facts are apparent from FIGS. 4(c) and 4(d). In particular, even if the air fuel ratio changes from a rich one to a lean one, the output of the integrating amplifier 11 remains, due to results of the preceding integration, as a signal the ionize and pump out oxygen from the detecting chamber C1. Accordingly, as the output of the integrating amplifier 11 is delivered to the pump cell 1, the rate that the air fuel ratio within the detecting chamber C1 is rich remains high and accordingly the rate that the output of the comparator 10 is a Hi signal remains high for a period of time after the air fuel ratio has changed from a rich one to a lean one. However, since in actuality the air fuel ratio in the path of exhaust gas is already lean, wherein such a period of time after the air fuel ratio changed from a rich one to a lean one, the rate that the air fuel ratio within the detecting chamber C1 is lean becomes high, that is, the rate that the output of the comparator 10 is a Lo signal becomes high. Accordingly, the rate that the integrating amplifier 11 integrates with a coefficient of the inverted polarity, that is, with a negative coefficient, increases. Consequently, the output voltage of the integrating amplifier 11 becomes lowered as seen in FIG. 4(d). Meanwhile, after the air fuel ratio has been changed to a lean one, control to return the air fuel ratio to the stoichiometric air fuel ratio is executed by an air fuel ratio controlling function which operates in response to the outputs of the comparator 12 and the adding circuit 13. Accordingly, exhaust gas is controlled so as to return from a lean state to a state of the stoichiometric air fuel ratio, and the output voltage of the integrating amplifier 11 is rapidly lowered in such a manner as to harmonize with such a change in the exhaust gas. Finally, when the stoichiometric air fuel ratio of the exhaust gas is reached, the output voltage of the integrating amplifier 11 becomes zero.

However, even after the air fuel ratio becomes equal to the stoichiometric air fuel ratio from a lean ratio, the ratio will change further toward the rich side due to overshooting. However, similar to the case described above wherein the air fuel ratio changes from a lean one to a rich one, the output of the integrating amplifier 11 remains, due to the results of the preceding integration, as a signal to ionize and pump out oxygen from the detecting chamber C1. Accordingly, as the output of the integrating amplifier 11 is delivered to the pump cell 1, the rate that the air fuel ratio within the detecting chamber C1 is lean remains high and accordingly, the rate that the output of the comparator 10 is a Lo signal still remains high for a period of time after the air fuel ratio has changed from a lean one to a rich one.

Then, when the rate of the rich air fuel ratio within the detecting chamber C1 becomes equal to the rate that the air fuel ratio within the detecting chamber C1 is lean, the duty of the output of the comparator 10 becomes 50%, and accordingly the output of the integrating amplifier 11 becomes essentially constant. In particular, when the output of the integrating amplifier 11 is positive, exhaust gas is in a lean state and the air fuel ratio within the detecting chamber C1 is changing from a rich one to a lean one. Then, when the exhaust gas changes from a rich state to a lean state, the pump cell voltage begins to act to ionize and pump oxygen into the detecting chamber C1 and while the air fuel ratio within the detecting chamber C1 is changing within the vicinity of the stoichiometric air fuel ratio, the exhaust gas becomes richer. Then, such change of the exhaust gas to a richer state is stopped and an action to make the exhaust gas leaner is accomplished again by control in response to a signal from the comparator 15 so as to make the air fuel ratio leaner as described hereinbelow, thereby facilitating air fuel ratio control within the vicinity of the stoichiometric air fuel ratio.

As the outputs of the comparator 10 and the integrating amplifier 11 change in such a manner as described above, the output of the adding circuit 13 changes as shown by the waveform of FIG. 4(e) while the output of the comparator 15 changes as seen from the waveform of FIG. 4(f). Here, as also seen from FIG. 4(e), the output waveform of the adding circuit 13 has a form similar to the output waveform of the integrating amplifier 11 and hence similar to the waveform of the change in the air fuel ratio of the exhaust gas, and the output of the comparator circuit 15 changes from a Hi signal to a Lo signal or from a Lo signal to a Hi signal when the air fuel ratio coincides with the stoichiometric air fuel ratio.

Accordingly, the output of the comparator 15 contains information regarding the stoichiometric air fuel ratio and is used as a signal for making the air fuel ratio richer when it is a Hi signal, but when it is a Lo signal, it is used as a signal for making the air fuel ratio leaner.

Meanwhile, the output of the adding circuit 13 contains information regarding a linear air fuel ratio and is used for control to attain an air fuel ratio other than the stoichiometric air fuel ratio (for example, for control to attain a particular lean air fuel ratio).

It is to be noted that only if the stoichiometric air fuel ratio is to be detected, the integrating amplifier 11 with positive and negative power sources may be replaced by a controlling means with an inversion-type power source which is constructed so as to output a fixed negative voltage when the output of the comparator 10 is a Hi signal and to output a fixed positive voltage when the output of the comparator 10 is a Lo signal. Also where such a controlling means with an inversion-type power source as described just above is employed, the direction of current flow in the resistor 17 changes when the air fuel ratio is equal to the stoichiometric air fuel ratio. Accordingly, detection of the stoichiometric air fuel ratio can be attained by detecting the change-over point of the direction of current flow in the resistor 17. It is to be added that in this instance the voltage detecting circuit 12 and the adding circuit 13 are unnecessary and can be omitted.

Otherwise, an inverter may be connected to a subsequent stage of the comparator 10 while the integrating amplifier 11 with positive and negative power sources or such a controlling means with an inversion-type power source as described above is constructed so as to output a positive voltage signal when a Hi signal is outputted from the comparator 10 and to output a negative voltage signal when a Lo signal is outputted from the comparator 10.

To the contrary, the integrating amplifier 11 with positive and negative power sources or such a controlling means with an inversion-type power source as described above may be constructed so as to output a positive voltage signal when the output of the comparator 10 without an inverter is a Hi signal and to output a negative voltage signal when the output of the comparator 10 without an inverter is a Lo signal. In this case, however, the pump electrode 3A of the pump cell 1 is grounded and the pump electrode 3B is connected to the integrating amplifier 11 with positive and negative power sources or the controlling means with an inversion-type power source.

Obviously, many modifications and variations of the present invention are possible in light of the above teachings. It is therefore to be understood that within the scope of the appended claims, the present invention may be practiced otherwise than as specifically described herein.

What is claimed is:

1. An air fuel ratio detecting device for a combustion engine, comprising:
   a cell unit having a detecting chamber, a diffusion hole defined within said cell unit for fluidically communicating an exhaust conduit of said engine with said detecting chamber, and a reference chamber fluidically communicating with an atmosphere;
   a sensor cell provided within said cell unit for producing a first output signal in response to a difference between the concentration of oxygen within said detecting chamber and the concentration of oxygen within said reference chamber;
   a first comparator for comparing said first output signal with a reference value and for producing a second output signal having one of two logic levels;
   integrator means for integrating said second output signal and for producing a control signal having a predetermined polarity depending upon a particular one of said two logic levels of said second output signal;
   a pump cell responsive to said control signal for moving oxygen ions in one of two directions with respect to said detecting chamber;
   a resistor interposed between said integrator means and said pump cell for detecting control current flow of said control signal;
   a second comparator for detecting the direction of said control current and for producing a comparator signal;
   stoichiometric air fuel ratio detecting means responsive to said comparator signal for producing a lean state signal or a rich state signal in response to said direction of said control current; and
   air fuel ratio detecting means responsive to a voltage value across said resistor for producing a linear air fuel ratio signal representing an air fuel ratio of an air fuel mixture burned within said engine.

2. An air fuel ratio detecting device according to claim 1, wherein:
   said sensor cell includes a sensor electrode, located on one of a pair of opposite side walls of said sensor cell, which is opposed to a detecting chamber into which exhaust gas is introduced, and a reference electrode located on the other side wall of said sensor cell which is opposed to said reference chamber into which reference gas is introduced, and
   said pump cell has one of a pair of opposite side walls thereof opposed to a path of exhaust gas from an engine combustion chamber and the other side wall thereof opposed to said detecting chamber,
   said pump cell having said diffusion hole formed therein so as to provide communication between said path of said exhaust gas and said detecting chamber,
   said pump cell also having a pair of pump electrodes located on said opposite side walls thereof.

3. An air fuel ratio detecting device according to claim 2, wherein said pump electrodes are disposed around an entrance and an exit of said diffusion hole.

4. An air fuel ratio detecting device according to claim 2, wherein one of said components of said sensor cell and pump cell is zirconia.

5. An air fuel ratio detecting device according to claim 2, wherein one of said sensor electrode and said reference electrode provided on said sensor cell, and said pump electrodes provided on said pump cell, are made of platinum.

6. An air fuel ratio detecting device according to claim 5, wherein said sensor electrode, said reference electrode and said pump electrodes each have a large number of pores formed therein.

7. An air fuel ratio detecting device according to claim 1, wherein said cell unit has a heater provided therefor.

* * * * *